US010055544B2

(12) United States Patent
Powell

(10) Patent No.: US 10,055,544 B2
(45) Date of Patent: Aug. 21, 2018

(54) PATIENT CARE PATHWAY SHAPE ANALYSIS

(71) Applicant: IMS Health Incorporated, Danbury, CT (US)

(72) Inventor: David Powell, Stoke-on-Trent (GB)

(73) Assignee: IMS Health Technology Services Limited, London (GB)

( * ) Notice: Subject to any disclaimer, the term of this patent is extended or adjusted under 35 U.S.C. 154(b) by 539 days.

(21) Appl. No.: 14/310,191

(22) Filed: Jun. 20, 2014

(65) Prior Publication Data

US 2015/0370967 A1 Dec. 24, 2015

(51) Int. Cl.

*G16H 10/60* (2018.01)
*G06F 19/00* (2018.01)
*G06Q 50/22* (2018.01)
*G16H 50/20* (2018.01)

(52) U.S. Cl.

CPC ........... *G06F 19/322* (2013.01); *G06Q 50/22* (2013.01); *G16H 10/60* (2018.01); *G16H 50/20* (2018.01)

(58) Field of Classification Search

None

See application file for complete search history.

(56) References Cited

U.S. PATENT DOCUMENTS

2002/0082865 A1* 6/2002 Bianco ................ G06F 19/3481 705/2
2002/0152097 A1* 10/2002 Javors .................... G06Q 40/02 705/2
2003/0023461 A1* 1/2003 Quintanilla .......... A61B 5/0002 705/3
2003/0216939 A1* 11/2003 Bito ....................... G06Q 50/22 705/2
2004/0039710 A1* 2/2004 McMillan .............. G06Q 10/04 705/400
2004/0078240 A1* 4/2004 Katz ..................... G06F 19/322 705/3
2004/0122702 A1* 6/2004 Sabol ..................... G06Q 50/22 705/2
2005/0182659 A1* 8/2005 Huttin ................... G06F 19/327 705/2
2006/0224416 A1* 10/2006 Lloyd .................... G06Q 50/24 705/2
2007/0106533 A1* 5/2007 Greene .................. G06Q 10/10 705/2
2007/0179349 A1* 8/2007 Hoyme ............... G06F 19/3418 600/300
2008/0059224 A1* 3/2008 Schechter ............ G06F 19/322 705/2
2008/0183500 A1* 7/2008 Banigan ................. G06Q 50/24 705/3
2008/0195420 A1* 8/2008 Ramelson ............. G06F 19/322 705/3

(Continued)

*Primary Examiner* — Jonathan Ng
*Assistant Examiner* — Rachelle L Reichert
(74) *Attorney, Agent, or Firm* — Fish & Richardson P.C.

(57) ABSTRACT

A method includes accessing data related to a series of patient events, and determining whether the data accessed is related to a specific condition. Care pathway data for the condition is generated in response to determining that the accessed data is related to the specific condition. The care pathways data for the condition is stored at a custom extension to a relational database.

19 Claims, 6 Drawing Sheets

Access data related to a series of patient events 502
Determine whether the data accessed is related to the treatment of a specific condition 504
Generate care pathway data related to the treatment of a specific condition 506
Store the care pathway data for the condition at one or more databases 508
Receive a query request 510
Access stored care pathway data 512
Provide query results 514

(56) References Cited

U.S. PATENT DOCUMENTS

2008/0201174 A1* 8/2008 Ramasubramanian ........................... G06F 19/3456 705/3
2009/0055221 A1* 2/2009 Loftus ................. G06F 19/3481 705/3
2009/0163774 A1* 6/2009 Thatha ................... G06Q 50/22 600/301
2009/0164248 A1* 6/2009 Hunt ..................... G06F 19/322 705/3
2009/0319292 A1* 12/2009 Warner ................. G06F 19/328 705/2
2010/0076786 A1* 3/2010 Dalton .................. G06F 19/322 705/3
2010/0076790 A1* 3/2010 Benja-Athon ........ G06F 19/322 705/3
2011/0077958 A1* 3/2011 Breitenstein ........... G06Q 10/10 705/2
2011/0144518 A1* 6/2011 Causevic ............ G06F 19/3443 600/544
2011/0166883 A1* 7/2011 Palmer ................... G06Q 10/10 705/3
2011/0213625 A1* 9/2011 Joao ...................... G06F 19/322 705/3
2011/0238434 A1* 9/2011 Froehlich .............. G06F 17/248 705/2
2013/0035958 A1* 2/2013 O'Keeffe ............... G06Q 10/10 705/3
2013/0191135 A1* 7/2013 Camacho .............. G06F 19/327 705/2
2014/0297240 A1* 10/2014 Duftler ............... G06F 19/3437 703/6

* cited by examiner

200

300

400

PATIENT CARE PATHWAY SHAPE ANALYSIS

BACKGROUND

Variations in patient care for the treatment, and or diagnosis of a particular condition often occur; two patients may be diagnosed with the same condition yet both patients may experience two completely different diagnosis and or treatment plans.

SUMMARY

In one aspect, data related to a series of patient events is accessed, and it is determined whether the data accessed is related to the treatment of a specific condition. Care pathway data for the condition is generated in response to determining that the accessed data is related to the treatment of a specific condition. The care pathway data for the condition is stored at one or more databases.

In another aspect, a query request is received from a user to access care pathway data. The stored care pathway data is accessed from the one or more databases and the query results are provided to the user. In yet another aspect, the care pathway data for the condition is generated by linking the one or more patient events related to the treatment of the condition. The linked patient events for the treatment of the condition are represented as a single value, and the single value is a care pathway shape. In another aspect, the care pathway data is a custom C# C# (or any other common language runtime (CLR) compatible programming language) data type. The C# (or any other CLR compatible programming language) data type can then be used to create a user-defined type (UDT) which can be installed in the Microsoft SQL Server database.

In yet another aspect, the query results are provided to the user at high speeds to facilitate a dynamic query-response dialogue between the user and the care pathway data. In another aspect, a patient event is identified as a point of interest event, and the point of interest event is flagged in the care pathway data. The query request may return results at varying levels of detail by performing transformations on the pathway shape data type to allow some event types and points of interest to be ignored when grouping pathway shapes. For example, a subset of event types and points of interest flags out of those recorded may be returned in the query results.

In another aspect, some implementation may provide a system comprising one or more computers and one or more storage devices storing instructions that are operable, when executed by one or more computers, to cause the one or more computers to perform operations comprising accessing data related to a series of patient events, and determining whether the data accessed is related to the treatment of a specific condition. In response to determining that the accessed data is related to the treatment of a specific condition, generating care pathway data for the condition. The care pathway data for the condition is stored at one or more databases.

In yet another aspect, some implementations may provide a non-transitory computer-readable medium storing software comprising instructions executable by one or more which, upon such execution, cause the one or more computers to perform operations comprising accessing data related to a series of patient events and determining whether the data accessed is related to the treatment of a specific condition. In response to determining that the accessed data is related to the treatment of a specific condition, generating care pathway data for the condition. The care pathway data for the condition is stored at one or more databases.

DETAILED DESCRIPTION

Figure 1:
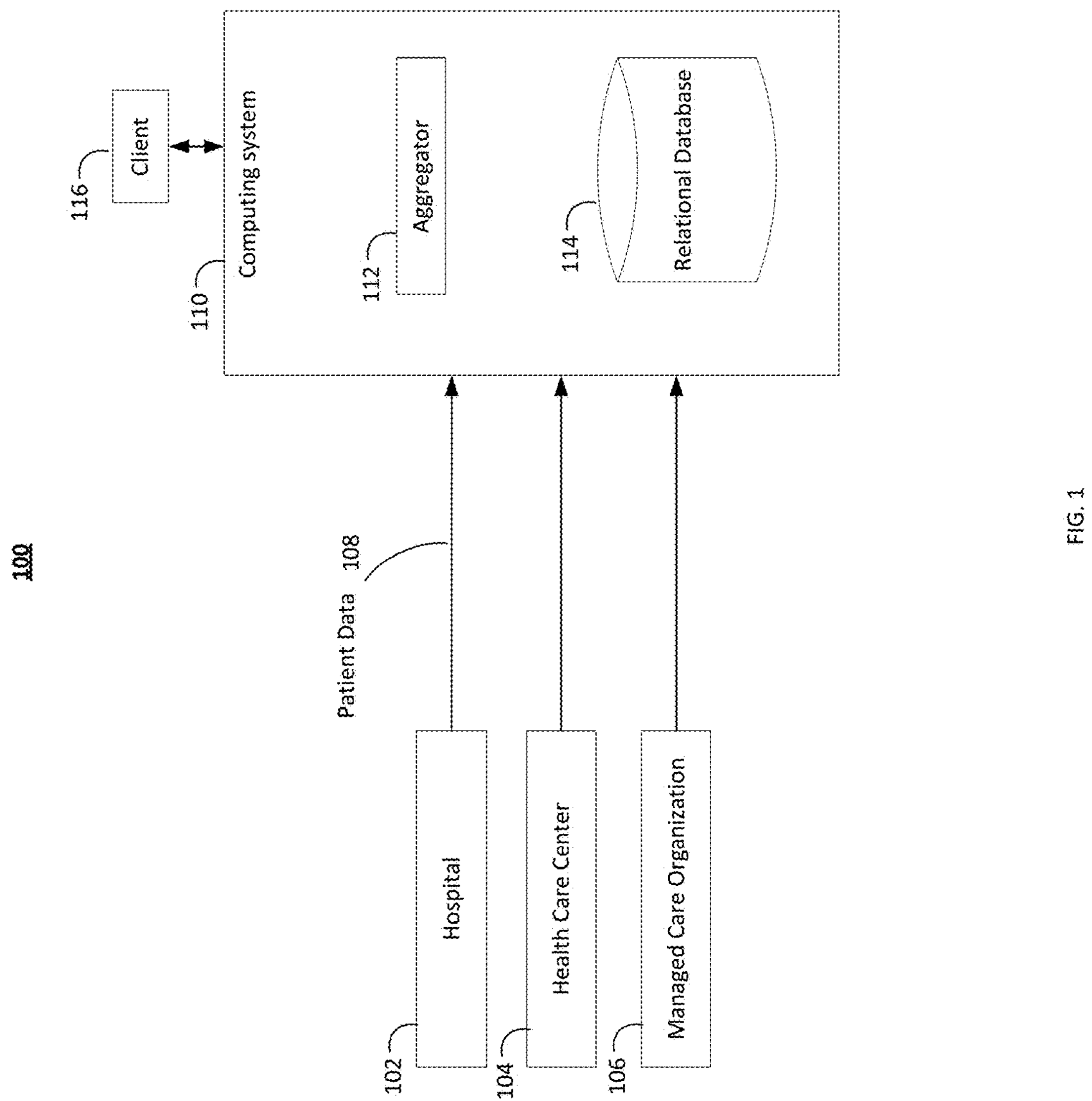
FIG. 1 illustrates an example of an analytical infrastructure implemented in a computing system 100.

This disclosure generally describes computer-implemented methods, software, and systems for storing patient care event pathways within a custom database and facilitating high performing dynamic queries on the patient care event pathways stored within the database. The computer-implemented methods, systems and software provide a web-based interactive tool for exploring the patterns and variations that occur in patient care pathways.

A patient pathway is a sequence of events that a patient may experience for the treatment of a particular medical condition. These events may include medical procedures, diagnoses or medical test results. Variations in patient care pathways for the treatment of a particular condition often occur; two patients may be diagnosed with the same medical condition yet both patients may experience two completely different care pathways. A treatment event may be an outpatient attendance, an attendance of a hospital appointment, an attendance of a screening, an in-patient stay, a pathology test, or any other suitable health event. It is important to monitor the different treatment pathways experienced by different patients for the treatment of the same condition in order to identify the variations in the treatment received. Identifying the variation in the care pathway experienced by different patients provides insight into both the cost and clinical effectiveness of a specific pathway. Identifying an effective pathway for the treatment of a particular condition may potentially lead to the development of standardized care pathways for specific conditions.

Traditionally, individual treatment events and care pathways would be stored in distinct database tables. Conducting a search through the database to identify a care pathway would therefore involve the construction of each care pathway at run time by forming representations of pathways through a joined SQL query on the two distinct tables of a relational database. On the other hand, the present disclosure involves generating a care pathway shape as a new custom user-defined type (UDT) extension to the SQL Server database. The analysis of care pathway shapes may be conformed into a comparison based on values in a single column, where the pathway shape is represented as a single unique value in a custom database column. The pathway shape is a pre-calculated unique data value. Conducting a search through this custom database allows pathway shapes to be compared and aggregated in exactly the same way one could achieve with simple SQL data types such as numbers or dates. This ensures that the grouping can be optimized by the database engine and the queries submitted by the web application front end can be executed far quicker than a traditional method. By facilitating querying through the use of the standard comparison and aggregation features of SQL against the new UDT the analysis of care pathway shapes can occur at very high speeds. These speeds may be fast enough to facilitate an interactive run-time dialogue with an end user.

FIG. 1 illustrates an example analytical infrastructure system implemented in a computing system 100. The computing system may be implemented as a data processing apparatus that is capable of providing the functionality discussed herein, and may include any appropriate combination of processors, memory, and other hardware and software that can receive appropriate medical data and process the data as discussed below. At a high-level, the illustrated example computing system 100 receives patient data from various institutes that provide healthcare to patients. The health care institutes may include hospitals 102, health care centers 104, and managed care organizations 106. In some implementations, pharmaceutical prescription information may be received from pharmacies that dispense medication to patients. It is important to understand that the system may be configured to preserve patient privacy and will not store nominative data in an aggregated database, but only de-identified data. Nominative data for an individual can be compared to the relevant aggregated data, but this may be achieved by using aggregated values in the individual patient application, not by keeping nominative records for multiple patients in a single database. Also, the integration of data from sources other than the user and their medical professionals may be achieved on a de-identified basis except in the instance that the individual gives permission to use their identity information (name, location, gender and age) for the purpose of providing them with their information from another source.

The patient data 108 may include patient identifying data, for example, the patient data may include the name, gender, age, and address for patients treated at the health care institutes. The patient data may also include patient event data. As described earlier, a patient event may be an outpatient attendance, an attendance of a hospital appointment, an attendance of a screening, an in-patient stay, a pathology test, or any other suitable health event. This data may be provided to the computing system 100 on a daily basis. In other implementations, the patient event data is provided to the computing system 100 monthly.

For illustrative purposes, computing system 100 will be described as including an aggregator 112 and a relational database 114. However, the computing system 100 may be any computing platform capable of performing the described functions. The computing system 100 may include one or more servers that may include hardware, software, or a combination of both for performing the described functions. Moreover, the aggregator 112 and the relational database 114 may be implemented together or separately in hardware and/or software.

One or more clients 116 may interface with the computing system 100 to request search queries of the relational database of pathway shapes. In some implementations, the one or more clients 116 may include a web browser that provides Internet-based access to the computing system 100. Through the web browser, a user of a client 116 (e.g., a wholesaler, a retail outlet, a health information analyst, or a prescriber) may perform a pathway analytical query.

There may be any number of clients 116 associated with, or external to, the example computing system 100. While the illustrated example computing system 100 is shown in communication with one client 116, alternative implementations of the example computing system 100 may communicate with any number of clients 116 suitable to the purposes of the example computing system 100. Further, the term "client" and "user" may be used interchangeably as appropriate without departing from the scope of this disclosure. Moreover, while client 116 is described in terms of being used by a single user, this disclosure contemplates that many users may share the use of one computer, or that one user may use multiple computers.

The illustrated client 116 is intended to encompass computing devices such as a desktop computer, laptop/notebook computer, wireless data port, smartphone, personal digital assistant (PDA), tablet computing device, one or more processors within these devices, or any other suitable processing device. For example, the client 116 may include a computer that includes an input device, such as a keypad, touch screen, or other device that can accept user information, and an output device that conveys information associated with the operation of the computing system 100. The input device may be used by client 116 to provide instructions to computing system 100 that computing system 100 can execute to provide query results requested by client 116 from the various data that computing system 100 receives.

Figure 2:
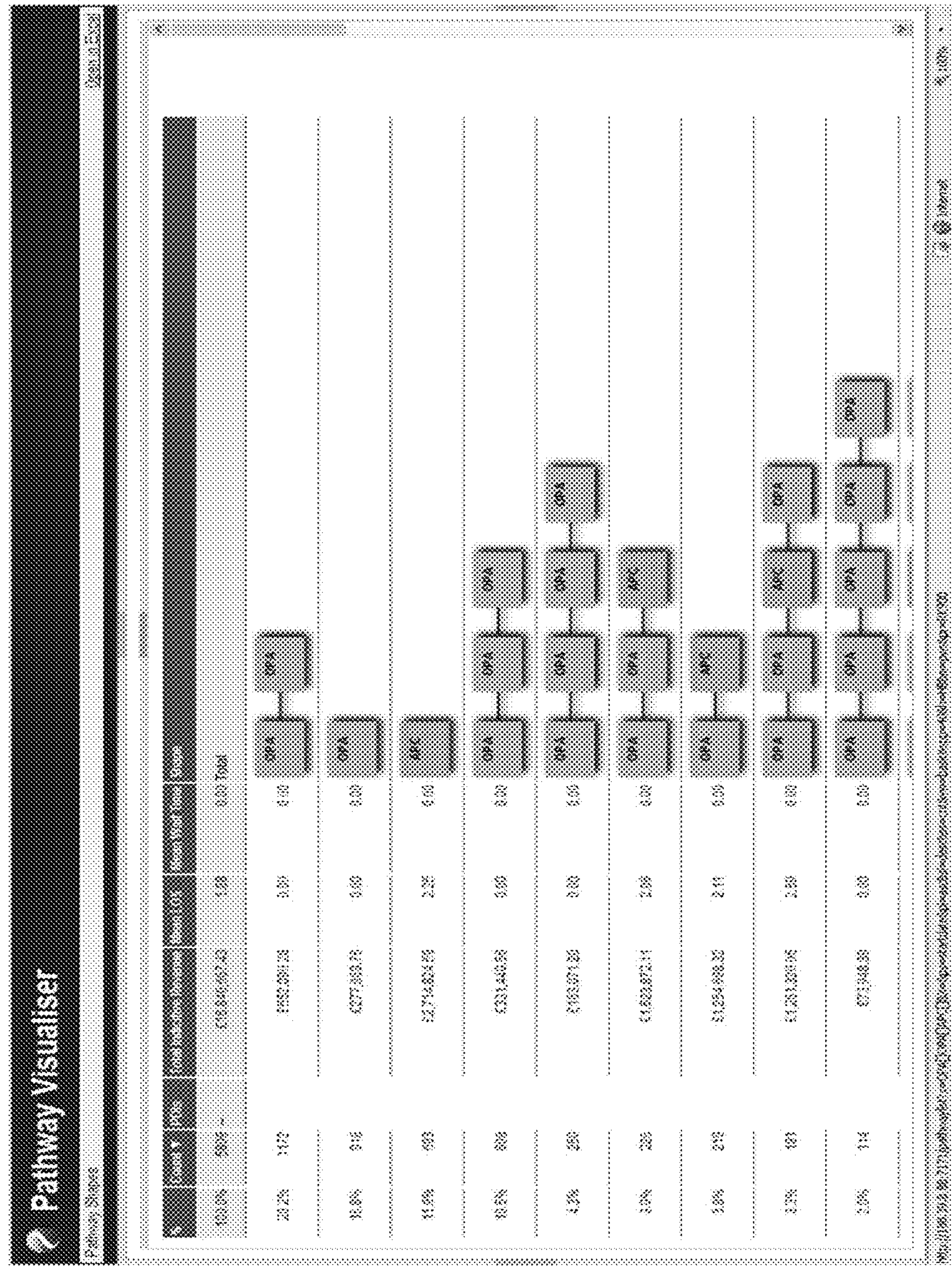
FIGS. 2-4 illustrate example user interfaces for user interaction with a web-application of a care pathway offering.
Figure 3:
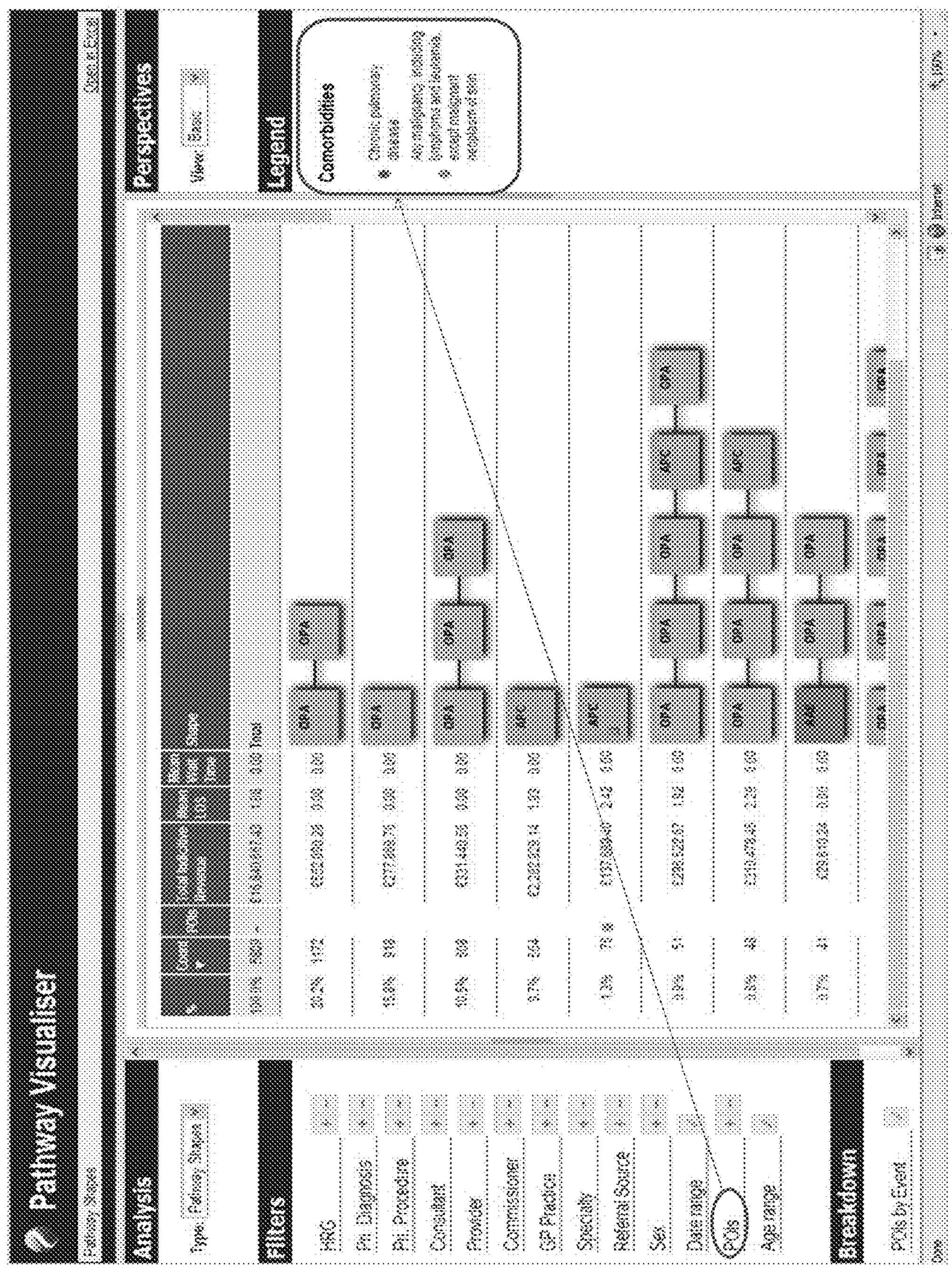
Figure 4:
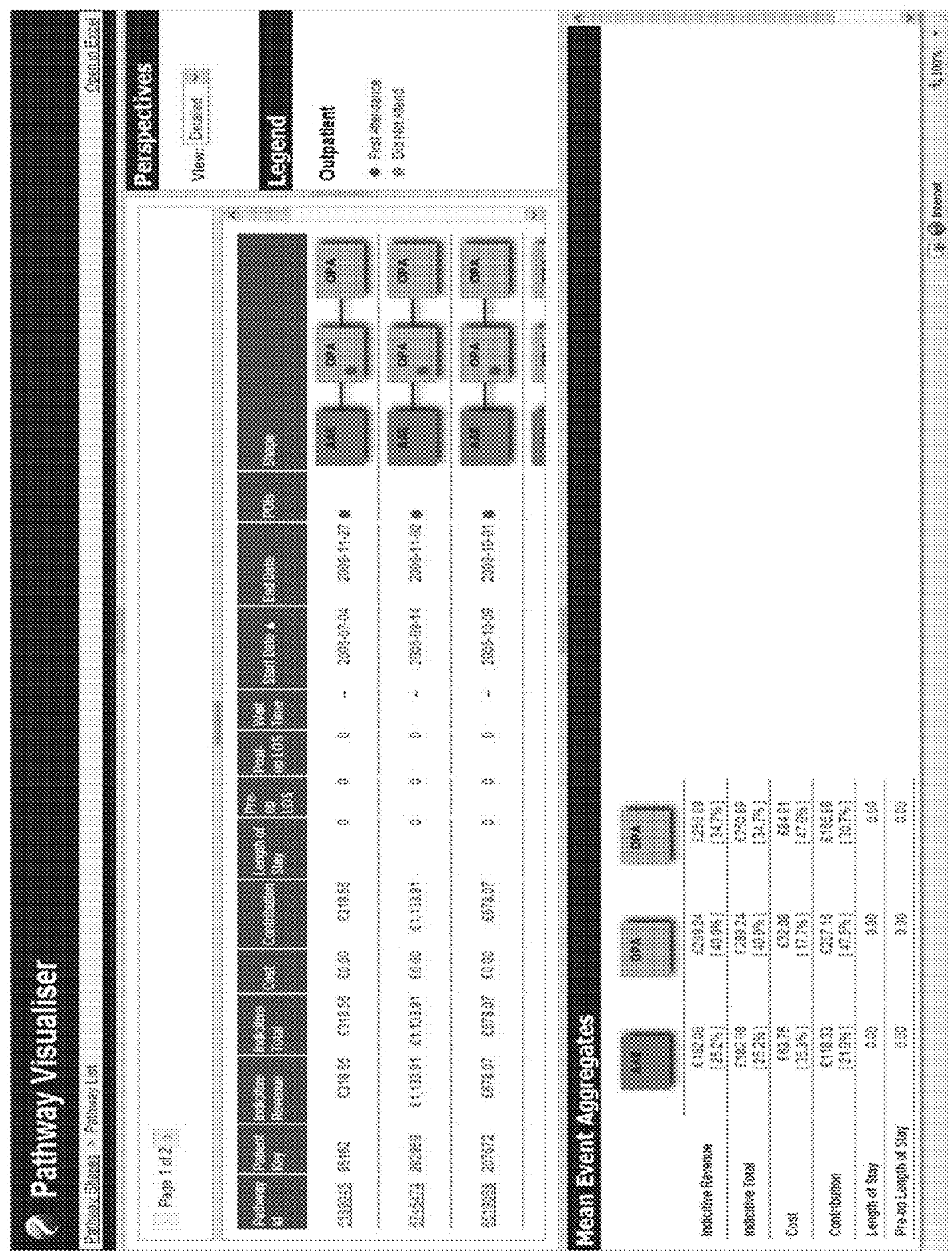

FIGS. 2-4 illustrate example user interfaces for user interaction with an application of a care pathway offering. A user may be a client 116 that accesses the web-application to the computing system 100. The user may be an information technologist at a health care institute that is interested in the trends that occurs across patient care. The information technologist may query the data received by the computing systems at the analytical infrastructure. In some implementations, the user may be internal IMS consultants that wish to query the data received by the computing systems. Interface 200 may be displayed when a user logs into a secure connection with the care pathway application offering. The user may log into the application by providing a user specific user name and password. The webpage may be specific to individual users of the application, that is, the webpage generated is specific to user. In some implementations, the user may have the option to customize the information displayed on the web page. In these implementations, the webpage may include a "Customize Page" tab displayed on the home page.

As illustrated in FIG. 2, the user interface may include a "count" column the "count" may display the number of patient care pathways that have been completed by an organization selected. The "count" of patient care pathways for a particular condition may be expressed as a percentage. FIG. 2 illustrates a count of 5809 patients. The user interface may also include a total indicative revenue column, a mean wait time column, and finally may include the care pathway shape column. The care pathway shape column shows the outpatient attendances (OPA) and admitted patient care events (APC).

FIG. 3 is an example user interface 300 that may be displayed when the user selects a context's menu on the user interface. In some examples, the context menu may be a hidden menu. The menu may be displayed as a panel at the left hand side of the user interface. As illustrated, the panel displayed on the left hand side of the user interface includes one or more filters. The filters may be used to filter the pathway shapes which will be displayed. Some filters may relate to attributes of the patient, for example, age, sex, etc. Some other filters may relate to the events, for example, specialty, primary diagnosis, primary procedure, etc. The patient pathways may be grouped based on different pathway shapes. The user has the ability to toggle each filter on and off. The interface shown in FIG. 3 may be displayed when the user toggles the "points of interest" filter on to query the data at varying levels of detail. The user interface 300 displays any point of interest events that occur in the patient care event pathway shapes. In some implementations, the points of interest events that may occur in the pathway shapes are displayed in a legend on the right hand side of the user interface.

As illustrated at the right hand side panel in FIG. 3, the user has selected a "basic view." The user has the ability to toggle through the views displayed on the user interface in the right hand panel. The user may switch views between the "finance" view, the "clinical" view and "detailed" view. When the user selects the "finance" view, the financial information is displayed in the right hand panel and the user can see the financial information related to a particular patient care pathway. When the user selects the "clinical" view, clinical information is displayed in the right hand panel.

FIG. 4 is an example user interface 400 that may be displayed when the user selects to view the patients that had the same care pathway shape. The user may select to view an individual pathway by clicking on the pathway ID, as illustrated in FIG. 4. When the pathway ID is selected, the user interface displays the individual patients that experienced the selected pathway. For example, the pathway AAE-OPA-OPA may show the details for the individual 41 patients that have experienced this pathway shape. The user may select an individual user to view the patient event details for the particular selected individual care pathway. The information may include patient demographics, for example, patient sex, patient identifier, etc. The information may also include the name of the consultant or physician, the procedure done, diagnoses, costs, length of stay, etc.

Figure 5:
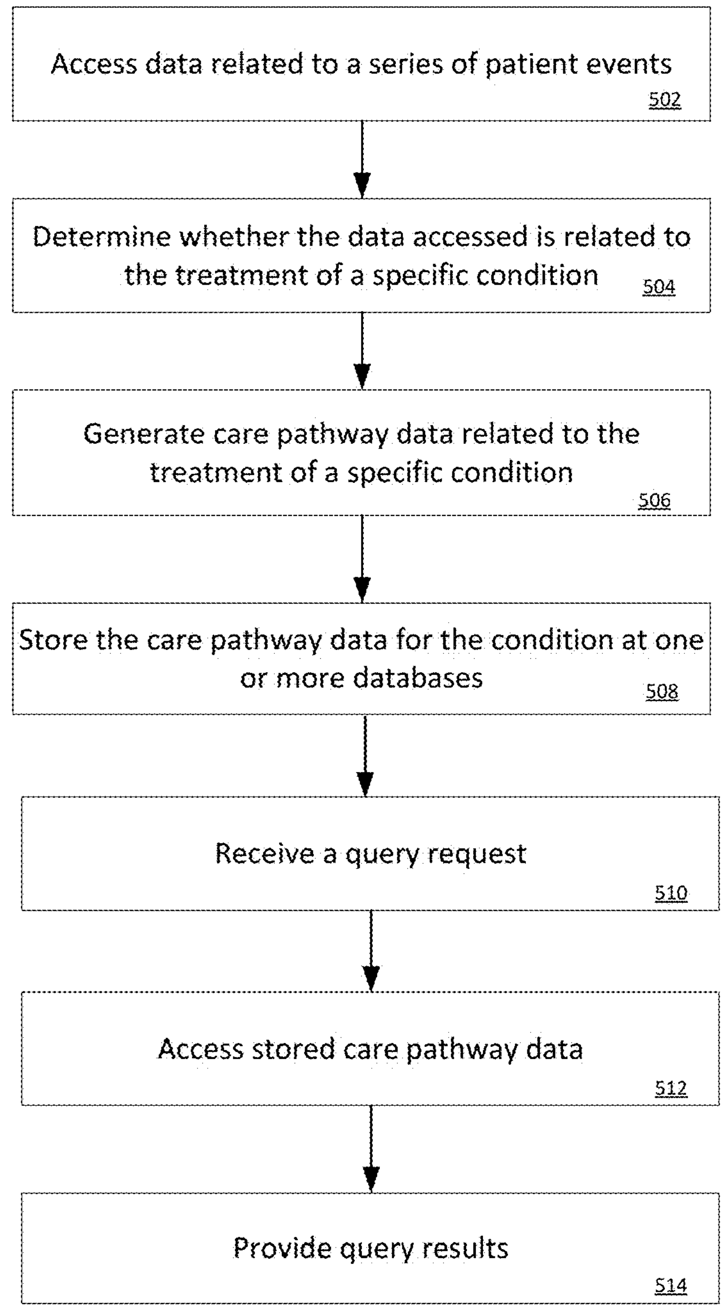
FIG. 5 is a flow chart of an example process for storing care pathway data for a particular condition based on accessed data of patient events.

FIG. 5 is a flow chart of a process 500 for storing care pathway data for a particular condition based on accessed data of patient events. The computing systems at the analytical infrastructure may access data related to a series of patient events (502). In some implementations, the patient events may be accessed by one or more processors at the computing systems. The patient event data may be received as patient data from one or more health care institutes. The health care institutes may include health centers, hospitals, and managed care organizations. A patient event may be an outpatient attendance, an attendance of a hospital appointment, an attendance of a screening, an in-patient stay, or a medical test. The patient event data for a particular patient may be associated with the patient identification number. In some implementations, the patient event data received for a particular patient may include patient events related to the treatment of one condition. For example, the patient event data may include the patient events experienced by a patient that is being treated for a torn meniscus. In this example, the patient event data may include an initial visit, a surgery, a follow up visit, and physical therapy visits. In some other implementations, the patient event data received for a particular patient may include events related to the treatment of one or more conditions and therefore the patient event data represents more than one care pathway for the patient. For example, the patient event data may include patient events experienced by a patient with diabetes that broke his arm. In this example, the patient event data may include the patient's routine diabetic checkups, and may further include events associated with the patient's broken arm and thus two distinct care pathways are represented by the event data.

The computing systems at the analytical infrastructure may determine whether the data accessed is related to the treatment of a specific condition (504). The computing systems may analyze the accessed patient event data to determine if the event is related to a specific condition. In some implementations, the computing systems at the analytical infrastructure may analyze the patient data received from one or more health care institutes to determine if the event data is related to the treatment of a specific condition. In some examples, the patient event data may be tagged by the computing systems at the health care institute. The patient event data may be tagged by the computing care institute prior to receiving the data at the computing systems at the analytical infrastructure. The tag may include details about the patient event, including the condition for which the patient received treatment. In other implementations, the computing systems at the analytical infrastructure may perform analytics on the accessed patient data to determine whether the data accessed is related to the treatment of a specific condition. For example, the computing systems at the analytical infrastructure may identify patient event data related to a particular patient identification number, and determine if the patient events are related based on patient event data trends observed over past time periods. In some implementations, the computing systems at the analytical infrastructure may use a pathway generator to determine patient events that are related to the treatment of a specific condition.

The computing systems at the analytical infrastructure may generate care pathway data for the condition, in response to determining that the accessed data is related to the treatment of a specific condition (506). The care pathway data for the specific condition may be generated by linking the one or more patient events related to the treatment of the specific condition. The computing systems at the analytical infrastructure may generate a pathway shape for patient events for the treatment of a specific condition. This pathway shape may be stored as a unique value as care pathway data. The care pathway data for the specific condition may be generated by linking the one or more patient events related to the treatment of the specific condition. The computing systems at the analytical infrastructure may generate an event shape for each patient event in the care pathway for the treatment of a specific condition. The computing systems may then aggregate the event shapes for the string of patient events to form a pathway shape. This pathway shape may be stored as a unique value as care pathway data. In some implementations, the aggregator 112 at the analytical infrastructure may string the patient events related to the treatment of a specific condition together. The patient events may be strung together in sequential order based on the date and time associated with the patient event. The computing systems at the analytical infrastructure, including the aggregator, may be associated with a relational database management system. The aggregator and the relational database are programmed using structured query language programming (SQL) programming. The aggregator may accept the individual patient events as SQL scalar functions, and aggregates the patient event data as data strings. The aggregator may return data strings as care pathway data. The care pathway data may be provided as a newly defined bespoke C# (or any other CLR compatible programming language) data type.

In some implementations, the care pathway data may include a long sequence of related patient events. The long sequence of related patient events may be considered as one or more sets of patient events. In these implementations, the aggregator 112 may string each set of patient events related to the treatment of the specific condition. The aggregator may then aggregate the strings of each set of events together to generate the care pathway data.

The care pathway data for the condition is stored at one or more databases (508). The care pathway data is stored as a unique distinct value. The care pathway data may be stored as a pathway shape. In some examples, the care pathway data is stored as an extension in the relational database 114. In other examples, the care pathway is stored in a separate custom database.

The computing systems at the analytical infrastructure may receive a query request, submitted by a user, to access care pathway data (510). A user may be a client 116 that accesses the web-application to the computing system 100. The user may be an information technologist at a health care institute that is interested in the trends that occurs across patient care. The information technologist may query the data received by the computing systems at the analytical infrastructure. In some implementations, the user may be an internal IMS consultant that wishes to query the data received by the computing systems. A search query may request the care pathway for treatment of a particular disease. The user may have the ability to customize the query to include age groups of patients treated, or the sex of patients treated, etc. The user may have the ability to otherwise customize the query request. For example, the user may have the ability to customize the query request to include or exclude one or more point of interest events along the care pathway. A point of interest event may be an event that is flagged in the care pathway for the treatment of a condition.

The computing systems at the analytical infrastructure may access the stored care pathway data (512). The care pathway data is stored as a unique value in a custom database. In some implementations, the care pathway data is stored as column type data. The column type data allows the care pathway data to be group and compared to other care pathway data that have the shape key attributes. The care pathway data type may be stored as a C# (or any other CLR compatible programming language) data type. The C# (or any other CLR compatible programming language) data type allows the care pathway data to be queried, compared and aggregated in exactly the same way that simple SQL data types, such as numbers or dates. At the query run time, the computing systems at the analytical infrastructure constructs SQL statements that query the care pathway data.

The computing systems at the analytical infrastructure may provide the query results to the user (514). The query results are provided to user at very high speeds. These speeds are fast enough to facilitate a real-time query-response dialogue with an end user who is submitting queries against a database which contains many millions of event records. The care pathway data is pre-calculated and is stored as a data type in a new custom database. This allows queries to be executed very quickly, and the search results provided at high speeds to the user. The query results may be displayed on the web-application of the analytical infrastructure as illustrated in FIGS. 2-4.

Figure 6:
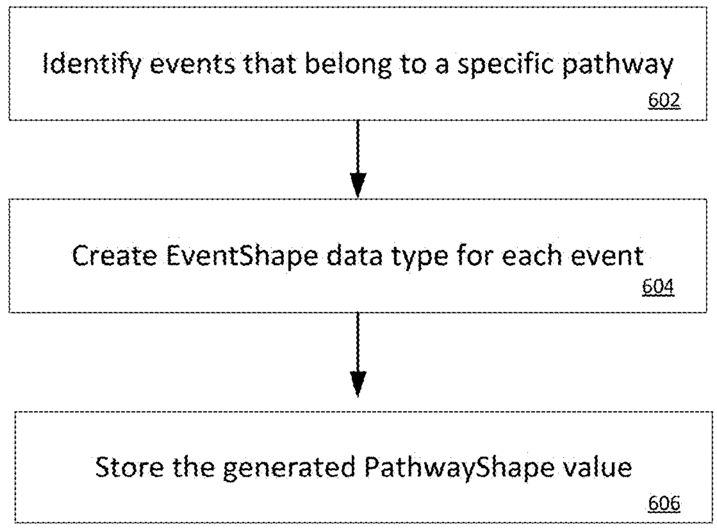
FIG. 6 is a flow chart of an example process for generating a pathway shape value.

FIG. 6 is a flow chart of a process 600 for generating a pathway shape value. The pathway shape for patient care events is stored in a database as a single unique value. The pathway shape is a pre-calculated unique data value. Storing the pathways shape is a single unique data value allows pathways to be compared and grouped together and otherwise analyzed.

The computing systems at the analytical infrastructure may identify events that belong to a specific pathway (602). The pathway may include a long sequence of related patient events. The computing systems at the analytical infrastructure may access the patient data that has been received from one or more health care institutes, such as, health centers, hospitals, and managed care organizations. The computing systems may be configured to store the patient identification as de-identified data. The patient data may include patient event data; a patient event may be an outpatient attendance, an attendance of a hospital appointment, an attendance of a screening, an in-patient stay, or a pathology test. The computing systems at the analytical infrastructure may identify the patient events related to a patient by a patient identification number. The patient events related to a particular patient may then be further analyzed by the computing systems at the analytical infrastructure to determine if all the events were related to the treatment of a particular condition, or related to a particular diagnosis.

For example, the patient event data associated with a pregnant woman who broke her leg while being pregnant will include patient events related to regular pregnancy checkups and may also include patient events related to the treatment of the broken leg. The computing systems at the analytical infrastructure may further analyze the patient event data related to the pregnant woman and identify the particular events that were related to the pregnancy and the particular events related to the broken leg. The computing systems at the analytical infrastructure may then tag the patient events for the pregnant woman related to the broken leg, these tagged events may then be associated with a pathway treatment for a broken leg. The computing systems at the analytical infrastructure may then tag the patient events related to the pregnancy; these tagged events may then be associated with a pathway for pregnancy. In some implementations, the computing systems at the analytical infrastructure may use a pathway generator that uses a configurable rule to determine patient events that are related to the treatment of a specific condition.

The computing systems at the analytical infrastructure may generate a custom event shape data type for each event (604). The custom event shape data type may be a C# (or any other CLR compatible programming language) data type. In some implementations, a SQL scalar function MakeEventShape may be used an entry point. The MakeEventShape can be called from a SQL select clause. The SQL scalar function MakeEventShape may accept SQL parameters and can then return a C# (or any other CLR compatible programming language) EventShape object. The EventShape C# data type may be used as a table column type. In some implementations, a patient event may be identified as a point of interest and the point of interest may be flagged. In these implementations, an arbitrary number of points of interest can be represented using a helper class.

The computing systems at the analytical infrastructure may store the pathway shape value in a database (606). The PathwayShape value is a C# (or any other CLR compatible programming language) data type and may be stored in a new custom database.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method comprising:

receiving, by one or more processors and from a client device, a query for pathway shapes for a particular medical condition;

accessing, by the one or more processors and from one or more healthcare data systems, treatment data for a plurality of patients receiving treatment for the particular medical condition, the treatment data for each patient indicating (i) a series of patient events for a particular patient receiving treatment for the particular medical condition, (ii) a particular sequence of patient events within the series of patient events;

generating, by the one or more processors, a respective care pathway shape for each of the plurality of patients, comprising:

determining, by one or more processors and for each of the patient events, one or more medical conditions associated with a particular patient event;

in response to determining the one or more medical conditions associated each of the patient events, generating, by the one or more processors and for each of the patient events, event shape descriptive of the one or more medical conditions associated with a particular patient event;

combining, by the one or more processors, the event shape for each of the patient events in accordance with the particular sequence of patient events within the series of patient events;

generating, by the one or more processors, a unique value representing the series of patient events based at least on combining the event shapes for each of the patient events in accordance with the particular sequence of patient events within the series of patient events; and storing, by the one or more processors, at a custom extension to a relational database, the unique value representing the series of patient events;

analyzing, by the one or more processors, the unique values of the care pathway shapes for the plurality of patients;

selecting, by the one or more processors and based on analyzing the unique values of the care pathway shapes for the plurality of patients, a subset of care pathway shapes from among the care pathway shapes for the plurality of patients, the subset of care pathway shapes comprising care pathway shapes that each share (i) two or more identical event shapes, and (ii) an identical sequence of the two or more identical event shapes within a corresponding series of patient events; and providing, by the one or more processors and for output to the client device responsive to the received query for pathway shapes for the particular medical condition, query results indicating the subset of pathway shapes.

2. The method of claim 1 wherein generating a care pathway data shape for the condition comprises linking each of the one or more patient events to the one or more medical conditions.

3. The method of claim 2 wherein the linked patient events, related to the one or more medical conditions, are represented as a single value.

4. The method of claim 1 wherein the care pathway data shape is represented as a custom C# data type value.

5. The method of claim 1 wherein the care pathway data shape is represented as a common language runtime (CLR) compatible programming language data type value.

6. The method of claim 1 wherein providing the query results for output to the client device comprises providing real-time query results in response to receiving the query request submitted by the user.

7. The method of claim 1 further comprising:

identifying a patient event as having a point of interest attribute; and grouping the care pathway shape data utilizing the point of interest attribute.

8. The method of claim 1 wherein:

The relational database comprises a structured query language (SQL) server database; and the unique value comprises a representation of a user-defined type (UTD) extension to the SQL server database.

9. The method of claim 8 wherein the unique value is stored in a single database column of the SQL database server.

10. A system comprising:

one or more computers and one or more storage devices storing instructions that are operable, when executed by one or more computers, to cause the one or more computers to perform operations comprising:

receiving, by one or more processors and from a client device, a query for pathway shapes for a particular medical condition;

accessing, by the one or more processors and from one or more healthcare data systems, treatment data for a plurality of patients receiving treatment for the particular medical condition, the treatment data for each patient indicating (i) a series of patient events for a particular patient receiving treatment for the particular medical condition, (ii) a particular sequence of patient events within the series of patient events;

generating, by the one or more processors, a respective care pathway shape for each of the plurality of patients, comprising: determining, by one or more processors and for each of the patient events, one or more medical conditions associated with a particular patient event;

in response to determining the one or more medical conditions associated each of the patient events, generating, by the one or more processors and for each of the patient events, event shape descriptive of the one or more medical conditions associated with a particular patient event;

combining, by the one or more processors, the event shape for each of the patient events in accordance with the particular sequence of patient events within the series of patient events;

generating, by the one or more processors, a unique value representing the series of patient events based at least on combining the event shapes for each of the patient events in accordance with the particular sequence of patient events within the series of patient events; and storing, by the one or more processors, at a custom extension to a relational database, the unique value representing the series of patient events;

analyzing, by the one or more processors, the unique values of the care pathway shapes for the plurality of patients;

selecting, by the one or more processors and based on analyzing the unique values of the care pathway shapes for the plurality of patients, a subset of care pathway shapes from among the care pathway shapes for the plurality of patients, the subset of care pathway shapes comprising care pathway shapes that each share (i) two or more identical event shapes, and (ii) an identical sequence of the two or more identical event shapes within a corresponding series of patient events; and providing, by the one or more processors and for output to the client device responsive to the received query for pathway shapes for the particular medical condition, query results indicating the subset of pathway shapes.

11. The system of claim 10 wherein generating a care pathway data shape for the condition comprises linking each of the one or more patient events to the one or more medical conditions.

12. The system of claim 11 wherein the linked patient events, related to the one or more medical conditions, are represented as a single value.

13. The system of claim 10 wherein the care pathway data shape is represented as a custom C# data type value.

14. The system of claim 10 wherein the care pathway data shape is represented as a common language runtime (CLR) compatible programming language data type value.

15. The system of claim 10 wherein providing the query results for output to the client device comprises providing real-time query results in response to receiving the query request submitted by the user.

16. The system of claim 10 further comprising:

identifying a patient event as having a point of interest attribute; and grouping the care pathway shape data utilizing the point of interest attribute.

17. A non-transitory computer-readable medium storing software comprising instructions executable by one or more which, upon such execution, cause the one or more computers to perform operations comprising:

receiving, by one or more processors and from a client device, a query for pathway shapes for a particular medical condition;

accessing, by the one or more processors and from one or more healthcare data systems, treatment data for a plurality of patients receiving treatment for the particular medical condition, the treatment data for each patient indicating (i) a series of patient events for a particular patient receiving treatment for the particular medical condition, (ii) a particular sequence of patient events within the series of patient events;

generating, by the one or more processors, a respective care pathway shape for each of the plurality of patients, comprising: determining, by one or more processors and for each of the patient events, one or more medical conditions associated with a particular patient event;

in response to determining the one or more medical conditions associated each of the patient events, generating, by the one or more processors and for each of the patient events, event shape descriptive of the one or more medical conditions associated with a particular patient event;

combining, by the one or more processors, the event shape for each of the patient events in accordance with the particular sequence of patient events within the series of patient events;

generating, by the one or more processors, a unique value representing the series of patient events based at least on combining the event shapes for each of the patient events in accordance with the particular sequence of patient events within the series of patient events; and storing, by the one or more processors, at a custom extension to a relational database, the unique value representing the series of patient events;

analyzing, by the one or more processors, the unique values of the care pathway shapes for the plurality of patients;

selecting, by the one or more processors and based on analyzing the unique values of the care pathway shapes for the plurality of patients, a subset of care pathway shapes from among the care pathway shapes for the plurality of patients, the subset of care pathway shapes comprising care pathway shapes that each share (i) two or more identical event shapes, and (ii) an identical sequence of the two or more identical event shapes within a corresponding series of patient events; and providing, by the one or more processors and for output to the client device responsive to the received query for pathway shapes for the particular medical condition, query results indicating the subset of pathway shapes.

18. The medium of claim 17 wherein generating a care pathway data shape for the condition comprises linking each of the one or more patient events to the one or more medical conditions.

19. The medium of claim 17 wherein providing the query results for output to the client device comprises providing real-time query results in response to receiving the query request submitted by the user.

* * * * *